United States Patent [19]

Yu et al.

[11] Patent Number: 4,973,688

[45] Date of Patent: Nov. 27, 1990

[54] PROCESS FOR THE PRODUCTION OF 1-N-DODECYLAZACYCLOHEPTAN-2-ONE

[75] Inventors: Lingchong Yu; Enjian Hou; Jin Li; Xixian Deng, all of Beijing, China

[73] Assignee: Beijing Normal University, Beijing, China

[21] Appl. No.: 451,160

[22] Filed: Dec. 15, 1989

[30] Foreign Application Priority Data

Apr. 24, 1989 [CN] China .................................. 89102672

[51] Int. Cl.$^5$ ............................................ C07D 223/10
[52] U.S. Cl. ...................................... 540/533; 540/485
[58] Field of Search .................................. 540/533, 485

[56] References Cited

U.S. PATENT DOCUMENTS 4,422,970 12/1983 Radadhyarsa et al. ............. 540/533
4,692,523 9/1987 Schorr et al. ...................... 540/533

*Primary Examiner*—Robert T. Bond
*Attorney, Agent, or Firm*—Birch, Stewart, Kolasch & Birch

[57] ABSTRACT

There is disclosed a method for the production of 1-n-dodecylazacycloheptan-2-one by reacting caprolactam with 1-bromododecane in the presence of a phase transfer catalyst under anhydrous conditions using a non-poisonous hydrocarbon as solvent. The method is a one-pot synthesis employing solid-liquid phase transfer catalysis.

10 Claims, No Drawings

PROCESS FOR THE PRODUCTION OF 1-N-DODECYLAZACYCLOHEPTAN-2-ONE

BACKGROUND OF THE INVENTION

1. Field of the Invention

The invention relates to a process for the production of 1-n-dodecylazacycloheptan-2-one and more particularly relates to an improved process of systhesis of 1-n-dodecylaza cycloheptan-2-one using tetrabutylammonium bromide or triethylbenzylammonium chloride as phase transfer catalyst under anhydrous solid-liquid phase conditions.

2. Background of the Prior Art 1-n-dodecylazacyoloheptan-2-one is in the form of colourless, odorless oily liquid having the following formula:

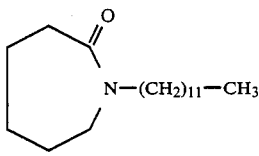

It is well known as a penetration enhancer. When incorporated into pharmaceutical preparations or into nutriment cosmetics, it can greatly enhance the penetration of active components through the skin, thus diminishing the amounts of active ingredients used in pharmaceutical preparation or nutriments used in cosmetics.

This compound is suitable for agricultural use with insecticides, fungicides and herbicides. It can also be used as a dying enhancer for fiber or synthetic fiber to enhance dye penetration of fibers and to allow the dying process to take place at lower temperature in a shortened period. Therefore, this compound has wide and important industrial applications.

The conventional process of preparing 1-alkyl substituted azacycloalkan-2-ones is based on the reaction of alkali salts of azacycloalkan-2-ones with alkylating agents; See for example, L. Ruzicka, Helv. Chim. Acta 4, 472(1921); C. S. Marvel et al., J.Org.Chem.22,1065 (1957); U.S. Pat. Nos. 3,989,815, 3,989,816 and 4,122,170. In the prior art, the alkali salts of azacycloalkan-2-ones are prepared by treating azacycloalkan-2-one with alkali metals or alkali metal hydrides in the presence of an inert solvent under nitrogen atmosphere. This prior art method, however, is uneconomical because of the costly alkali metals, alkali metal hydrides, and the large amount of solvent required.

EP No. 0095096 discloses an improved method of synthesis of 1-substituted azacycloalkan-2-ones wherein the N-alkylation is carried out in the presence of phase transfer catalysts. The reaction is run from about 20° C. to about 50° C. and over a period of from 50 hours to about 200 hours. The solvent used in the reaction includes aromatic hydrocarbons such as benzene, toluene, and aliphatic hydrocarbons.

This method, however, also possesses many disadvantages. Firstly, a liquid-liquid phase transfer catalysis, having an aqueous phase and an organic phase, is used in the process. Due to the presence of water, coextraction of some water of hydration often occurs during the reaction, resulting in a low yield of the end product and the reaction being completed over a long period of time. Secondly, the solvents toluene, which is poisonous and of a high boiling point, and ether, which are inflammable and explosive, is used in the process, resulting in the production of the compound being not only costly, but also harmful to workers. Therefore, the process is not suitable for large-scale production in industry.

SUMMARY OF THE INVENTION

The present invention provides an improved process for the production of 1-n-dodecylazacycloheptan-2-one. According to the invention, the subject compound is prepared by reacting caprolactam with an alkyl halide, which is used as alkylating agent, in the presence of mixed bases. The reaction is carried out under anhydrous conditions in a nonpoisonous hydrocarbon solvent with a low boiling point, and the reaction is catalysed by a phase transfer catalyst.

DETAILED DESCRIPTION OF THE INVENTION

As the reaction according to the invention is conducted in a heterogeneous reaction system including a solid phase and a liquid phase, a phase transfer catalyst is employed to perform the reaction. Such a catalyst used herein includes tetrabutyl-ammonium bromide and triethylbenzylammonium chloride; the prefered catalyst is tetrabutylammonium bromide. The amount of catalyst used may vary from about 2 to about 3 mole percent, the prefered amount being about, 3 mole percent.

The alkylating agent according to the invention is 1-bromododecane (or 1-chlorododecane). The molar ratio of this agent to caprolactam may vary between about 0.8:1 and about 1.2:1, and the prefered ratio is 1:1. At this ratio, the two starting materials can react completely and efficiently; thus, a large excess amount of alkylating agent is not required as in EP No. 0095096.

The base used in the invention is a mixture of an anhydrous carbonate of an alkali metal and pulverized hydroxide of an alkali metal. The prefered base is a mixture of anhydrous potassium carbonate and potassium hydroxide. The molar ratio of caprolactam to anhydrous potassium carbonate to sodium (or potassium) hydroxide is about 1 to 0.7–0.9 to 1.8–3, and the prefered ratio is about 1 to 0.7 to 1.8.

The solvent used in the invention includes cyclohexane, n-hexane and petroleum ether. These solvents are superior to conventional solvents, for example, toluene, used in the prior art. Because these solvents are nonpoisonous, they are harmless to workers and do not contaminate environment. In addition, these solvents have lower boiling points, so the step of removing these solvents can be carried out at a lower temperature.

The reaction may be conveniently run from about 40° C. to about 70° C. and over a period of from about 5 hours to about 7 hours. The reaction time depends upon the temperature at which the reaction is carried out and the amount of catalyst used. When compared with the prior art, however, the reaction time of the present invention is still many times shorter.

A comparision between the present invention and the prior art is shown in Table 1.

TABLE 1

| | In the present invention | in the prior art |
|---|---|---|
| Reaction time (hr) | 5–7 | 30–150 |
| Temperature (° C.) | 40–70 | 70–115 |
| solvent used | nonpoisonous | poisonous |
| Yield (%) | >92 | 40–70% |
| Purity of product | | |

TABLE 1-continued

| (%) | >99 | <98 |
| --- | --- | --- |

It is evident from Table 1 that the process used in the present invention is much more advantageous in many respects than those used in the prior art.

The reaction is carried out in a flask equipped with a funnel, reflux condenser and a mechanical stirrer. The reaction temperature is controlled with a water bath.

Thin-layer chromatography (TLC) is used to monitor the course of the reaction. The reagents used in the TLC include:

Silica Gel G (200 mesh, produced by Qing Dao Marine Chemical Factory);
Sodium salt of carboxymethyl cellulose (CMC)
Petroleum ether (60°–90° C.), (A.R.)
Ethyl acetate (A.R.)
Preparation of plates To 10 g of silica gel G is added 35 ml of a 0.5% aqueous solution of the sodium salt of carboxymethyl cellulose. These were mixed homogeneously. The obtained paste is then poured onto a piece of plate (2.5 cm × 7.5 cm) and spread out with a glass rod to avoid the presence of air bubbles. The dried chromaplates are then kept in a desiccator for later use.

Development of plates

After the sample is added on the chromaplate, it is eluted with an eluate of ethyl acetate and petroleum ether (3:7,v/v). After development, the plate is dried with a warm-air blower. The dried plate is allowed to stand in a closed tank containing iodine crystals over the tank bottom. The spots are revealed as brown stains. Then the RF value of the sample is measured. It is known that the RF value for caprolactam is 0.04, so the completion of the reaction can be determined from the appearence of a spot corresponding to RF=0.04.

The following examples are provided to describe the invention in further detail. These examples are intended to illustrate rather than to limit the invention.

EXAMPLE 1

Preparation of 1-n-dodecylazacycloheptan-2-one at a bath temperature of 55° C.

117 g of caprolactam (1.033 mole), 10 g of tetrabutylammonium bromide (0.03 mole), 100 g of anhydrous potassium carbonate (0.7 mole, dried for 2 hrs at 120 C.), 100 g of pulverized sodium hydroxide (2.5 mole), and 1 L of cyclohexane were placed in a flask equipped with a funnel, reflux condenser and a mechanical stirrer. To this mixture were added dropwise a solution of 250 ml of 1-bromododecane (1.033 mole) and 250 ml of cyclohexane with vigorous stirring over one-half hour at a bath temperature of 55° C. The stirring was continued; in the meanwhile thin-layer chromatography was used to monitor the course of the reaction, and it was found that the reaction was completed after 7 hours. The reaction mixture was then cooled to room temperature and filtered. The filtrate was washed with water (3×500 ml) to remove remaining caprolactam. The organic phase was dried over anhydrous magnesium sulfate. The filtrate was evaporated using a rotary film evaporator to remove cyclohexane (which can be used again), and the residue was distilled at reduced pressure to yield 270 g of colorless, odorless, transparent liquid product (yield: 92.8%), b,p.200–201 C/0.7 mmHg.

EXAMPLE 2

Preparation of 1-n-dodecylazacycloheptan-2-one at bath temperature of 60° C.

117 g of caprolactam (1.033 mole), 100 g of anhydrous potassium carbonate (dried for 2 hrs at 120° C.), 1 g of pulverized potassium hydroxide, 10 g of tetrabutylammonium bromide and one liter of cyclohexane.were placed in a flask equipped with a funnel, reflux condenser and a mechanical stirrer. While vigorously stirring, to this mixture were added in a dropwise manner 250 ml of 1-bromododecane (1.033 mole) and 250 ml of cyclohexane through the funnel at a bath temperature of 60° C. The addition was finished over one-half hour. While continuing to stir the reaction mixture, the reaction was monitored via thin-layer chromatography. The reaction was determined to have been completed five hours later. Then the mixture was cooled to room temperature, and was filtered. The filtrate was washed three times with water (500 ml for each time) to wash away residual caprolactam. The organic phase was dried over anhydrous magnesium sulfate overnight, and was fitered again. The filtrate was evaporated to remove cyclohexane (which can be used again); the residue was then distilled at reduced pressure, and yielded 272 g of colorless, odorless transparent liquid product (yield: 94%), b.p.200–201 C/0.7 mmHg.

While certain preferred embodiments of the present invention have been described above, it is not intended to limit the invention to such embodiments. Various modifications may be made thereto without departing from the scope and spirit of the present invention, as set forth in the following claims.

What we claim is:

1. A process for the production of 1-n-dodecylazacyclo heptan-2-one, comprising1reacting caprolactam with 1-btomododecane (or 1-chlorododecane) in the presence of a mixed base and a phase transfer catalyst, the reaction being solid-liquid phase transfer catalysis and carried out under anhydrous conditions in a hydrocarbon solvent.

2. A process as claimed in claim 1, wherein said base is a mixture of an anhydrous carbonate of an alkali metal and pulverized hydroxide of an alkali metal.

3. A process as claimed in claim 1 or claim 2, wherein said base is a mixture of anhydrous potassium carbonate and pulverized potassium or sodium hydroxide.

4. A process as claimed in claim 1, wherein said hydrocarbon solvent is cyclohexane, n-hexane or petroleum ether.

5. A process as claimed in claim 1, wherein said phase transfer catalyst is tetrabutylammonium bromide or triethylbenzylammonium chloride.

6. A process as claimed in claim 1, wherein the reaction is carried out at a temperature range from 40° C. to 70° C.

7. A process as claimed in claim 6, wherein the reaction is carried out at a temperature range from 45° C. to 60° C.

8. A process as claimed in claim 1, which also comprises a step of removing residual caprolactam from the crude product.

9. A process as claimed in claim 8, wherein the removal of caprolactam is carried out by washing the filtrate with water.

10. A process for the production of 1-n-dodecylazacycloheptan-2-one by reacting caprolactam with an alkylating agent, wherein the reaction is carried out in a solvent of cyclohexane, n-hexane or petroleum ether.

* * * * *